US011446586B2

(12) United States Patent
Thomas et al.

(10) Patent No.: US 11,446,586 B2
(45) Date of Patent: Sep. 20, 2022

(54) SEPARATION AND PURIFICATION OF FURAN CARBOXYLATES

(71) Applicant: Teknologian tutkimuskeskus VTT Oy, Espoo (FI)

(72) Inventors: David Thomas, Espoo (FI); Juha Linnekoski, Hyvinkää (FI)

(73) Assignee: TEKNOLOGIAN TUTKIMUSKESKUS VTT OY, Espoo (FI)

(*) Notice: Subject to any disclaimer, the term of this patent is extended or adjusted under 35 U.S.C. 154(b) by 155 days.

(21) Appl. No.: 16/967,430

(22) PCT Filed: Feb. 11, 2019

(86) PCT No.: PCT/FI2019/050098
§ 371 (c)(1),
(2) Date: Aug. 5, 2020

(87) PCT Pub. No.: WO2019/155127
PCT Pub. Date: Aug. 15, 2019

(65) Prior Publication Data
US 2021/0086100 A1 Mar. 25, 2021

(30) Foreign Application Priority Data
Feb. 9, 2018 (FI) .................................. 20185118

(51) Int. Cl.
B01D 3/00 (2006.01)
B01D 3/10 (2006.01)
C07D 307/68 (2006.01)

(52) U.S. Cl.
CPC ............. B01D 3/10 (2013.01); C07D 307/68 (2013.01)

(58) Field of Classification Search
CPC ........... B01D 3/00; B01D 3/10; C07D 307/68
See application file for complete search history.

(56) References Cited

U.S. PATENT DOCUMENTS

2013/0345448 A1* 12/2013 Shaikh ................ C07D 307/46
549/485
2016/0311790 A1 10/2016 Janka et al.

FOREIGN PATENT DOCUMENTS

| FI | 126387 B | 11/2016 |
| JP | 2008127282 A | 6/2008 |
| WO | WO W02013191938 A1 | 12/2013 |
| WO | WO W02013191944 A1 | 12/2013 |
| WO | WO 2015030590 A1 | 3/2015 |
| WO | WO W02016076711 A1 | 5/2016 |
| WO | WO2016166421 A1 | 10/2016 |
| WO | WO2017019441 A1 | 2/2017 |

OTHER PUBLICATIONS

Werpy et al.: Top Value Added Chemicals from Biomass. 2004, vol. 1, pp. 26-28.

* cited by examiner

Primary Examiner — Prem C Singh
Assistant Examiner — Brandi M Doyle
(74) Attorney, Agent, or Firm — Laine IP Oy; Mark W. Scott

(57) ABSTRACT

According to an example aspect of the present invention, there is provided a method for separating and purifying furan carboxylates from a crude reaction mixture comprising furans, by utilizing high vacuum distillation in a total heating environment.

10 Claims, 2 Drawing Sheets

SEPARATION AND PURIFICATION OF FURAN CARBOXYLATES

FIELD

The present invention relates to a separation and purification method of furan carboxylates from furoic acids and the reaction mixture resulting from the production process of furan carboxylates.

BACKGROUND

Furan carboxylates have been traditionally used for example in pharmacology, where its diethyl ester has showed a strong anesthetic activity. Furandicarboxylic acid (FDCA) is also a very powerful chelating agent. In medicine, it is for example used to treat kidney stones, but also in the preparation of grafts having biological properties similar to those of natural tissues, and which are characterized by a lack of rejection after transplantation.

FDCA has also been used as a basic monomer in the manufacture of polymers such as polyesters, polyamides, co-polymers or polyurethanes, for example for improving their mechanical properties. In polyesters, it is likely to be used in replacement of phthalates. In view of such a possibility, FDCA has been ranked among the 12 raw materials with the greatest industrial potential (Werpy and Peterson, 2004).

Furan carboxylates are also realistic alternative to terephthalic acid, which is a monomer used in polyethylene terephthalate production and used, for example, in plastic bottles. The bio-based furan carboxylate solution should therefore be both chemically efficient and environmentally sustainable.

Monocarboxylates such as 2-furoic acid finds uses as a monomer, preservative, flavouring agent, and it may have use in optic technologies. The 2-furoic acid esters can be used for example as bio-based fuel components.

Furan carboxylates, such as 2,5-furandicarboxylic acid (FDCA) can be produced from aldaric acids. For example WO 2016/166421 describes such method, wherein solid heterogenous catalysts are utilized. The resultant reaction mass typically contains unreacted raw material, small amounts of side reactions and the side product furoic acid (ester) in addition to FDCA (ester).

Much of the literature surrounding furandicarboxylic acid production does not focus any detail upon the purification step. Since an acid is typically produced then distillation is not possible, as the acid would decompose. FDCA esters possess a high boiling point (for example, approximately 186-190° C./13 Torr for the 2,5-dimethylfurandicarboxylic acid and 420° C. at normal pressure for 2,5-furandicarboxylic acid) that makes distillation a difficult procedure, typically resulting in very high levels of product decomposition. Additionally, problems lie in that a solid at room temperature (2,5-furandicarboxylic acid melting point 342° C. at normal pressure) is hard to distill without blocking the equipment.

Methods to produce FDCA include those using hydrogen WO 2013/191944 and US 2016/0311790 except these require dissolution solvent and temperatures up to 225° C. In addition, as example, WO 2015/030590 and WO 2013/191938 mention distillation as a separation method for FDCA. However, these publications do not disclose the use of high vacuum distillation in order to gently separate FDCA ester and avoid solidification of FDCA ester into the reaction vessel.

To suite for polymerization in high-end applications, the monomer itself needs to be of high purity, often greater than 99.5%. Impurities can cause, for example, failure of the polymerization and problems with the final product application. Thus, there is a need for an efficient and scalable method for separating the FDCA ester from the furoic acid, aldaric acid, aldaric acid esters and reaction mixture impurities.

SUMMARY OF THE INVENTION

The invention is defined by the features of the independent claims. Some specific embodiments are defined in the dependent claims.

According to an aspect of the present invention, there is provided a method for separating and purifying furan carboxylates from a crude reaction mixture comprising furans, aldaric acids and aldaric esters by utilizing high vacuum distillation in a total heating environment.

This and other aspects, together with the advantages thereof over known solutions are achieved by the present invention, as hereinafter described and claimed.

The method of the present invention is mainly characterized by what is stated in the characterizing part of claim 1.

Considerable advantages are obtained by means of the invention. FDCA is typically made as a mixture with furoic acid the side reaction. This is causing problems for all industrial players working in the arena. The present invention uses existing technology, and by separating the unreacted raw material before the distillation process, enables reuse of the raw material which gives a benefit in raw material cost savings and increased efficiency.

Next, the present technology will be described more closely with reference to certain embodiments.

EMBODIMENTS

The present technology provides an efficient separation and purification method for furan carboxylates, especially for furan acid ester and FDCA ester.

Figure 1:
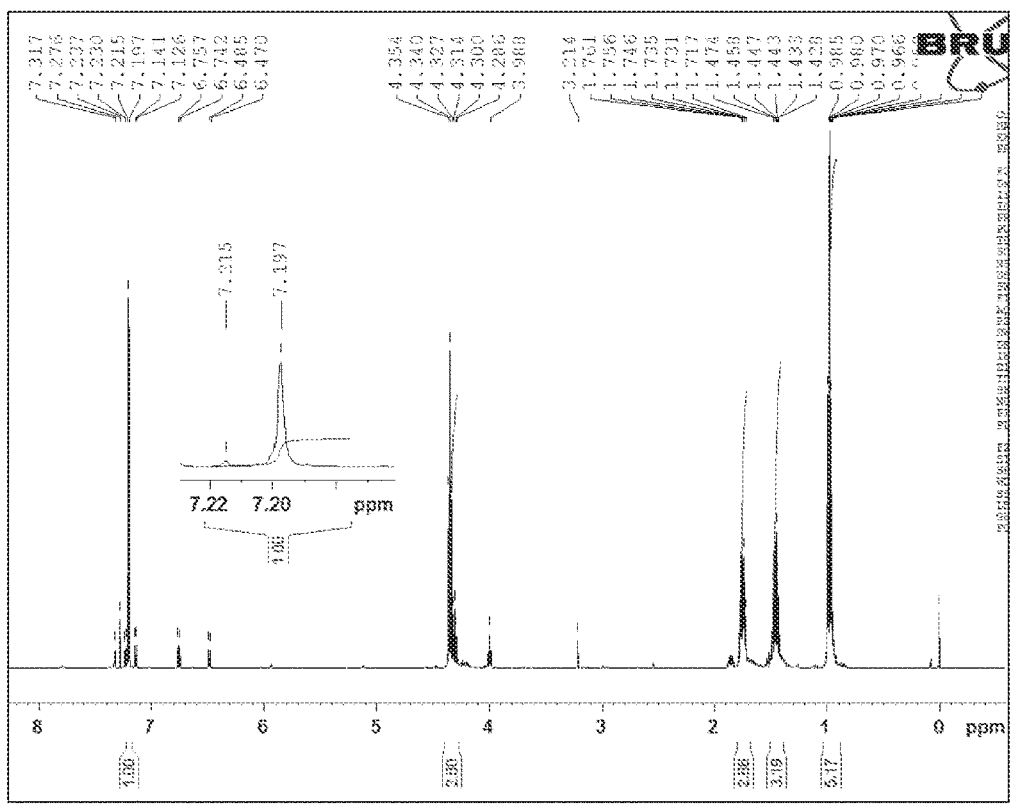
FIG. 1 is a 1H NMR diagram showing the FDCA peaks after distillation.
Figure 2:
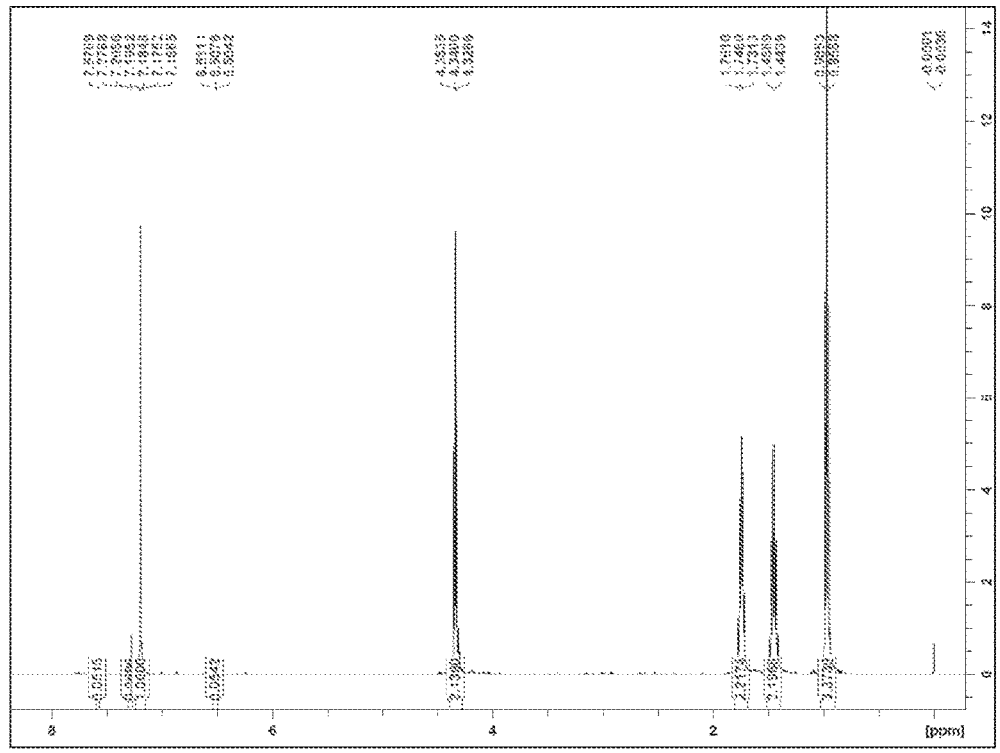
FIG. 2 is a 1H NMR diagram showing the FDCA reference compound peaks after distillation.
Figure 3:
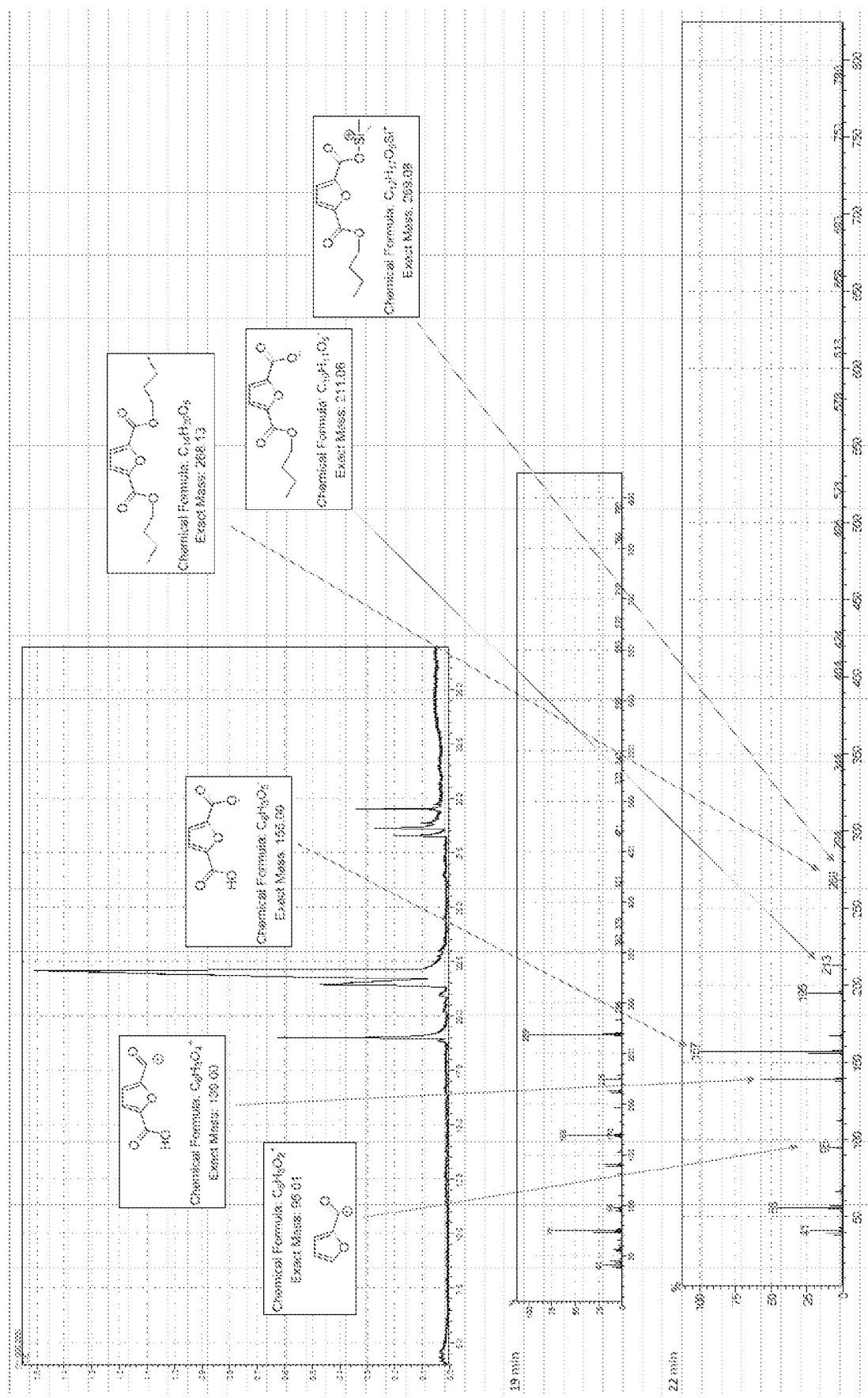
FIG. 3 is a GC-MS diagram of the FDCA after distillation.

The present invention is based on utilizing high vacuum distillation, which prevents the destruction of the FDCA ester due to high temperature needed for normal distillation. In addition, solidification of the product into the distillation equipment is avoided by keeping all the equipment hot, in other words by using a total heating environment, which enables the solidification to happen only in the receiving vessel.

According to one embodiment of the present invention, the present method includes separation and purification of furan carboxylates from a crude reaction mixture comprising furans, wherein the method includes the steps of:
  filtering of the crude reaction mixture to remove solids and to obtain a liquid phase,
  evaporating the liquid phase in temperature of 20-60° C. and pressure below 100 mbar,
  a highly concentrated mobile phase, or re-dissolving the evaporated liquid phase into an alcohol solvent,
  isolating furoic acid ester and FDCA ester from aldaric acids, aldaric ester and the solvent by high vacuum distillation in a total heating environment.

Isolation of the solids, mainly unreacted raw material or acid compounds is done for example by filtration and preferably prior to distillation in order to avoid the decomposition of materials that would have negative effect in the further purification steps.

According to one embodiment of the present invention, the evaporated liquid phase is re-dissolved into an alcohol solvent C1-C4 selected from methanol, ethanol, propanol or butanol.

According to one embodiment of the present invention, the high vacuum distillation is carried out at pressure lower than 4 mbar, preferably lower than 3 mbar, and most suitably lower than 1 mbar. High vacuum distillation minimizes thermal decomposition at elevated temperatures.

The total heating environment herein means that the distillation apparatus is not cold anywhere i.e. has no temperature gradients, but instead it is uniformly heated. By doing such, crystallization of the product into places which could block the distillation equipment is avoided and instead the solidification only happens in the receiving vessel.

One embodiment of the present invention is to use surround-heating distillation equipment. For example, Kugelrohr distillation is one good example of a distillation apparatus, which keeps the whole apparatus hot except the receiving vessel, which is ideal when distilling material with a high melting point at room temperature. By doing so, both furoic acid ester and FDCA ester can be isolated successfully and in an efficient manner.

Another advantage of the present invention is that no distillation aids is required.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

At least some embodiments of the present invention find industrial application in generating a full value chain from the forest industry, agriculture, or food industry side streams to platform chemicals and end applications. In principle, this chain comprises production of aldaric acids from aldoses and side-stream carbohydrates, converting the aldaric acids to dicarboxylic acids, which in turn are used as platform chemicals for various bio-based applications, such as bio-based polyesters and nylon. According to one example, the present method produces 2,5-Furandicarboxylic acid for use in the production of polyethylene furanoate. Efficient purification of the product is essential for further utilization and end-uses.

EXAMPLES

The GC-FID and GC-MS analyses were done with Shimadzu GC-1020 Plus Gas Chromatograph equipped with FID or MS analyser. The column used was ZB-5HT Inferno and the temperature program 100° C./1 min→10° C./min to 280° C./hold time 1 min→30° C./min to 350° C./hold time 5 min. When using FID-detector the following parameters where used injector temperature 320° C., detector temperature 380° C., carrier gas helium, pressure 100.2 kPa, total flow 103.8 ml/min, column flow 1.00 ml/min, linear velocity 27.5 cm/sec, purge flow 3.0 ml/min, injection volume 1.0 µl, split ratio 100. When using MS-detector the following parameters where used injector temperature 320° C., detector temperature 250° C., carrier gas helium, pressure 60 kPa, total flow 10 ml/min, column flow 1.00 ml/min, linear velocity 39 cm/sec, purge flow 3.0 ml/min, injection volume 1.0 µl, split ratio 50. All reaction fractions were silylated with standard methods prior to GC-FID and GC-MS analysis.

There are numerous ways to make FDCA or the FDCA ester. The purification method outlined below can be applied to each of these when the crude reaction product has been isolated. The crude oil can contain for example among others as main components 0.1-90 wt-% furoic acid or furoic acid esters, 0.1-90 wt-% FDCA or FDCA esters, 0.1-90 wt-% galactaric acid or galactaric acid esters and/or 0.1-90 wt-% glucaric acid or glucaric acid esters. For the purpose of illustration the synthesis of furandicarboxylic acid diester is outlined in detail in the separate patent FI 126387. Below are several examples for the production of purified FDCA ester after initial removal of the reaction catalyst.

1. Distillation of Crude Reaction Product FDCA Dibutyl Ester Using Kugelrohr at 5 Mbar The crude oil (1.29 g) was placed in a distillation bulb and the apparatus set-up for bulb-to-bulb distillation in the oven. The bulbs were set to stir between 1-40 rpm and a vacuum was gently applied. Over 5 minutes the vacuum was lowered to 5.1 mbar or lower. The temperature was increased in a stepwise until a yellow solid starts to appear the in the adjacent bulb at 164-170° C. The bulb was then slid out of the oven and cooled to about 0° C. The temperature was maintained until all FDCA dibutyl ester had been distilled across. The FDCA ester was isolated as an off-white solid, 24% recovery, $^1$H NMR: δ 0.9 (3H, m, CH$_3$), 1.4 (2H, m, —CH$_2$—), 1.73 (2H, m, —CH$_2$—), 4.3 (2H, m, —CH$_2$—), 7.2 (2H, s, Ar—H), GCMS: mz 268.

2. Distillation of Crude Reaction Product FDCA Dimethyl Ester Using Total Heat Environment at 3.4 Mbar The crude brown solid (320 mg) was placed in a distillation bulb and the apparatus set-up for bulb-to-bulb distillation in the oven. The bulbs were set to stir between 1-40 rpm and a vacuum was gently applied. Over 5 minutes the vacuum was lowered to 3.4 mbar or lower. The temperature was increased in a stepwise until a yellow solid started to appear in the adjacent bulb at 148-150° C. The bulb was then slid out of the oven and cooled to about 0° C. The temperature was maintained until all FDCA dibutyl ester had been distilled across. The FDCA ester was isolated as an off-white solid, 28% mass recovery of 97% based on GC-FID, 1H NMR: δ 3.9 (3H, m, CH3), 7.2 (2H, s, Ar—H), GCMS: mz 268.

3. Distillation of Crude Reaction Product FDCA Dibutyl Ester Using Total Heat Environment at 0-1 Mbar The crude reaction oil was charged to the distillation bulb and the apparatus set-up for bulb-to-bulb distillation in the oven. The bulbs were set to stir between 1-50 rpm and a vacuum was gently applied. Over 10 minutes the vacuum was lowered to 5 mbar to degas the system before dropping the vacuum to 0-1 mbar. The temperature was increased in a stepwise until a white solid material starts to solidify in the collection bulb at 140-145° C. The distillation was maintained until no further material distilled. The FDCA ester was afforded in 27.4% mass recovery 65% recovery (based on GC-FID yield), 1H NMR: δ 0.9 (3H, m, CH3), 1.4 (2H, m, —CH2-), 1.7 (2H, m, —CH2-), 4.3 (2H, m, —CH2-), 7.2 (2H, s, Ar—H), GCMS: mz 268. It should be noted that FDCA can be readily prepared from FDCA ester by the simple process of hydrolysis. No example is presented as someone with basic knowledge of the art can undertake such a procedure.

CITATION LIST

Patent Literature

WO 2016/166421
WO 2013/191944
US 2016/0311790
WO 2015/030590
WO 2013/191938
FI 126387

Non-Patent Literature

Werpy, T., Peterson, G., 2004. Top Value Added Chemicals from Biomass, Vol. 1 pp. 26-28.

The invention claimed is:

1. A method for separating and purifying furan carboxylates from a crude reaction mixture comprising at least furoic acid ester, 2,5-furandicarboxylic acid (FDCA) ester, an aldaric acid, and an aldaric acid ester, wherein the method comprises:
   filtering of the crude reaction mixture to remove solids and to obtain a liquid phase,
   evaporating the liquid phase at a temperature of 20-60° C. and at a pressure below 100 mbar,
   re-dissolving the evaporated liquid phase into an alcohol solvent,
   isolating the furoic acid ester and the 2,5-furandicarboxylic acid (FDCA) ester from the aldaric acid, the aldaric acid ester, and the alcohol solvent at a pressure lower than 4 mbar by vacuum distillation in a uniformly heated distillation apparatus.

2. The method according to claim 1, wherein before the evaporation, the liquid phase is first cooled, after which a formed precipitate is removed.

3. The method according to claim 1, wherein the alcohol solvent is selected from butanol, propanol, ethanol or methanol.

4. The method according to claim 1, wherein the vacuum distillation is carried out at a pressure lower than 4 mbar.

5. The method according to claim 1, wherein the vacuum distillation is carried out without any distillation aids.

6. The method according to claim 1, wherein the vacuum distillation is carried out by using surround-heating distillation equipment.

7. The method according to claim 1, wherein the vacuum distillation is carried out using Kugelrohr distillation equipment.

8. The method according to claim 1, wherein the vacuum distillation is carried out at pressure lower than 3 mbar.

9. The method according to claim 1, wherein the vacuum distillation is carried out at pressure lower than 1 mbar.

10. A method for separating and purifying a 2,5-furandicarboxylic acid (FDCA) ester from a mixture comprising at least the FDCA ester and an aldaric acid and/or an aldaric acid ester, wherein the method comprises:
    filtering of the crude reaction mixture to remove solids and to obtain a liquid phase,
    evaporating the liquid phase at a temperature of 20-60° C. and at a pressure below 100 mbar,
    re-dissolving the evaporated liquid phase into an alcohol solvent,
    isolating the FDCA ester from the aldaric acid and/or the aldaric acid ester and the alcohol solvent at a pressure lower than 4 mbar by vacuum distillation in a uniformly heated distillation apparatus.

* * * * *